United States Patent [19]
Hirabayashi et al.

[11] Patent Number: 5,780,284
[45] Date of Patent: Jul. 14, 1998

[54] CERAMIDE GLUCOSYLTRANSFERASE

[75] Inventors: Yoshio Hirabayashi; Shin-ichi Ichikawa, both of Saitama, Japan

[73] Assignee: The Institute of Physical and Chemical Research, Japan

[21] Appl. No.: 663,713

[22] Filed: Jun. 14, 1996

[30] Foreign Application Priority Data

Jun. 15, 1995 [JP] Japan .................................. 7-148472

[51] Int. Cl.[6] .................................................. C12N 9/10
[52] U.S. Cl. .................................................... 435/193
[58] Field of Search ...................................... 435/193

[56] References Cited

PUBLICATIONS

Brandli et al., "A Polarized Epithelial Cell Mutant Deficient in Translocation of UDP-galactose into the Golgi Complex", The Journal of Biological Chemistry, vol. 263, No. 31, pp. 16283–16290, Nov. 5, 1988.

Basu et al., "Enzymatic Synthesis of Ceramide–Glucose and Ceramide–Lactose by Glycosyltransferases from Embryonic Chicken Brain", The Journal of Biological Chemistry, vol. 243, No. 21, pp. 5802–5807, Nov. 10, 1968.

Ichikawa et al., "A Mouse B16 Melanoma Mutant Deficient in Glycolipids", Proc. Natl. Acad. Sci. USA, vol. 91, pp. 2703–2707, Mar. 1994.

Nozue et al., "Melanoma Antigen Expression and Metastatic Ability of Mutant B16 Melanoma Clones", Int. J. Cancer, vol. 42, pp. 734–738, 1988.

Radin, "Glucosylceramide in the Nervous System –A Mini–Review", Neurochemical Research, vol. 19, No. 5, pp. 533–540, 1994.

Inokuchi et al., "Preparation of the Active Isomer of 1–phenyl–2–decanoylamino–3–morpholino–1–propanol, Inhibitor of Murine Glucocerebroside Synthetase", Journal of Lipid Research, vol. 28, pp. 565–571, 1987.

Futerman et al., "Determination of the Intracellular Sites and Topology of Glucosylceramide Synthesis in Rat Liver", Biochem. J., vol. 280, pp. 295–302, 1991.

Durieux et al., "Solubilization of UDPglucose Ceramide Glucosyltransferase from the Golgi Apparatus", Biochimica et Biophysica Acta. vol. 1024, pp. 263–266, 1990.

Lannert et al., "Lactosylceramide is Synthesized in the Lumen of the Golgi Apparatus", FEBS Letters, vol. 342, pp. 91–96, 1994.

Jeckel et al., "Glucosylceramide is Synthesized at the Cytosolic Surface of Various Golgi Subfractions", The Journal of Cell Biology, vol. 117, No. 2, pp. 259–267, Apr. 1992.

Durieux et al., "Solubilization of UDPglucose–ceramide Glucosyltransferase from the Golgi Apparatus", Biochimica et Biophysica Acta, vol. 1024, pp. 263–266, 1990.

Trinchera et al., "Topography of Glycosyltransferases Involved in the Initial Glycosylations of Gangliosides", The Journal of Biological Chemistry, vol. 266, No. 31, pp. 20907–20912, Nov. 5, 1991.

Durieux et al. (Apr. 1990) Comparative Effects of Sulfhydryl Reagents on Membrane–Bound and Solubilized UDP–Glucose:ceramide Glucosyltransferase from Golgi Membranes. Evidence for Partial Involvement of a Thiol Group in the Nucleotide Sugar Binding Site of th.

Ngo et al. (Jan. 1994) Computational Complexity, Protein Structure Prediction, and the Levinthal Paradox, In The Protein Folding Problem and Tertiary Structure Prediction, Eds. Merz et al., Birkhauser, Boston, MA, pp. 491–495.

Schulte et al. (Nov. 1993) Ceramide UDP–galactosyltransferase from myelinating rat brain: Purification, cloning, and expression, Proc. Natl. Acad. Sci. USA 90: 10265–10269.

Paul et al. (Jan. 26,1996) Purification and Characterization of UDP–glucose:Ceramide Glucosyltransferase from Rat Liver Golgi Membranes, J. Biol. Chem. 271 (4): 2287–2293.

Ichikawa et al. (May 1996) Expression cloning of a cDNA for human ceramide glucosyltransferase that catalyzes the first glycosylation step of glycosphingolipid synthesis, Proc. Natl. Acad. Sci. USA 93: 4638–4643.

Vunnam et al. (Jan. 1979) Short chain ceramides as substrates for glucocerebroside synthetase, Biochimica et Biophysica Acta 573: 73–82.

*Primary Examiner*—Charles L. Patterson, Jr.
*Assistant Examiner*—Einar Stole
*Attorney, Agent, or Firm*—Wenderoth, Lind & Ponack

[57] ABSTRACT

The subject invention provides a novel ceramide glucosyltransferase having catalytic activity of glucose transfer from UDP-Glc to ceramide, and a nucleic acid sequence encoding the ceramide glucosyltransferase.

12 Claims, 4 Drawing Sheets

FIG. 2A

```
Met Ala Leu Leu Asp Leu Ala Leu Glu Gly Met Ala Val Phe Gly  15
Phe Val Leu Phe Leu Val Leu Trp Leu Met His Phe Met Ala Ile  30
Ile Tyr Thr Arg Leu His Leu Asn Lys Lys Ala Thr Asp Lys Gln  45
Pro Tyr Ser Lys Leu Pro Gly Val Ser Leu Leu Lys Pro Leu Lys  60
Gly Val Asp Pro Asn Leu Ile Asn Leu Glu Thr Phe Phe Glu His  75
Leu Asp Tyr Pro Lys Tyr Glu Val Leu Cys Val Gln Asp His Phe  90
Asp Asp Pro Ala Ile Asp Val Cys Lys Lys Leu Leu Gly Lys Tyr 105
Pro Asn Val Asp Ala Arg Leu Phe Ile Gly Gly Lys Lys Val Gly 120
Ile Asn Pro Lys Ile Trp Ile Cys Asp Ser Gly Tyr Glu Val Ala 135
Lys Tyr Asp Leu Ile Cys Asp Met Val Asn Gln Met Thr Glu Ile 150
Pro Asp Thr Leu Thr Asp Met Val Asn Gln Met Thr Glu Lys Val 165
Gly Leu Val His Gly Leu Pro Tyr Val Ala Asp Arg Gln Gly Phe 180
```

FIG. 2B

| | | | | | | | | | | | | | | |
|---|---|---|---|---|---|---|---|---|---|---|---|---|---|---|
| Ala | Ala | Thr | Leu | Glu | Gln | Val | Tyr | Phe | Gly | Thr | Ser | His | Pro | Arg | 195 |
| Tyr | Tyr | Ile | Ser | Ala | Asn | Val | Thr | Gly | Phe | Lys | Cys | Val | Thr | Gly | 210 |
| Met | Ser | Cys | Leu | Met | Arg | Lys | Asp | Val | Leu | Asp | Gln | Ala | Gly | Gly | 225 |
| Leu | Ile | Ala | Phe | Ala | Gln | Tyr | Ile | Ala | Glu | Asp | Tyr | Phe | Met | Ala | 240 |
| Lys | Ala | Ile | Ala | Asp | Arg | Gly | Trp | Arg | Phe | Ala | Met | Ser | Thr | Gln | 255 |
| Val | Ala | Met | Gln | Asn | Ser | Gly | Ser | Tyr | Ser | Ile | Ser | Gln | Phe | Gln | 270 |
| Ser | Arg | Met | Ile | Arg | Trp | Thr | Lys | Leu | Arg | Ile | Asn | Met | Leu | Pro | 285 |
| Ala | Thr | Ile | Ile | Cys | Glu | Pro | Ile | Ser | Glu | Cys | Phe | Val | Ala | Ser | 300 |
| Leu | Ile | Ile | Gly | Trp | Ala | Ala | His | His | Val | Phe | Arg | Trp | Asp | Ile | 315 |
| Met | Val | Phe | Met | Cys | His | Cys | Leu | Ala | Trp | Phe | Ile | Phe | Asp | 330 |
| Tyr | Ile | Gln | Leu | Arg | Gly | Val | Gln | Gly | Gly | Thr | Leu | Cys | Phe | Ser | 345 |
| Lys | Leu | Asp | Tyr | Ala | Val | Ala | Trp | Phe | Ile | Arg | Glu | Ser | Met | Thr | 360 |
| Ile | Tyr | Ile | Phe | Leu | Ser | Ala | Leu | Trp | Asp | Pro | Thr | Ile | Ser | Trp | 375 |
| Arg | Thr | Gly | Arg | Tyr | Arg | Leu | Arg | Cys | Gly | Gly | Thr | Ala | Glu | Glu | 390 |
| Ile | Leu | Asp | Val | | | | | | | | | | | | 394 |

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 1347 bases
      ( B ) TYPE: nucleic acid
      ( C ) STRANDEDNESS: double
      ( D ) TOPOLOGY: linear ( x i ) SEQUENCE DESCRIPTION: SEQ ID NO:1:

```
ATG  GCG  CTG  CTG  GAC  CTG  GCC  TTG  GAG  GGA  ATG  GCC  GTC  TTC  GGG          45
Met  Ala  Leu  Leu  Asp  Leu  Ala  Leu  Glu  Gly  Met  Ala  Val  Phe  Gly
 1                  5                   10                      15

TTC  GTC  CTC  TTC  TTG  GTG  CTG  TGG  CTG  ATG  CAT  TTC  ATG  GCT  ATC          90
Phe  Val  Leu  Phe  Leu  Val  Leu  Trp  Leu  Met  His  Phe  Met  Ala  Ile
                    20                  25                      30

ATC  TAC  ACC  CGA  TTA  CAC  CTC  AAC  AAG  AAG  GCA  ACT  GAC  AAA  CAG         135
Ile  Tyr  Thr  Arg  Leu  His  Leu  Asn  Lys  Lys  Ala  Thr  Asp  Lys  Gln
                    35                  40                      45

CCT  TAT  AGC  AAG  CTC  CCA  GGT  GTC  TCT  CTT  CTG  AAA  CCA  CTG  AAA         180
Pro  Tyr  Ser  Lys  Leu  Pro  Gly  Val  Ser  Leu  Leu  Lys  Pro  Leu  Lys
                    50                  55                      60

GGG  GTA  GAT  CCT  AAC  TTA  ATC  AAC  AAC  CTG  GAA  ACA  TTC  TTT  GAA         225
Gly  Val  Asp  Pro  Asn  Leu  Ile  Asn  Asn  Leu  Glu  Thr  Phe  Phe  Glu
                    65                  70                      75
```

| | | | | | | | | | | | | | | | |
|---|---|---|---|---|---|---|---|---|---|---|---|---|---|---|---|
| TTG | GAT | TAT | CCC | AAA | TAT | GAA | GTG | CTC | CTT | TGT | GTA | CAA | GAT | CAT | 270 |
| Leu | Asp | Tyr | Pro | Lys 80 | Tyr | Glu | Val | Leu 85 | Leu | Cys | Val | Gln | Asp | His 90 | |
| GAT | GAT | CCA | GCC | ATT | GAT | GTA | TGT | AAG | AAG | CTT | CTT | GGA | AAA | TAT | 315 |
| Asp | Asp | Pro | Ala 95 | Ile | Asp | Val | Cys | Lys 100 | Lys | Leu | Leu | Gly | Lys | Tyr 105 | |
| CCA | AAT | GTT | GAT | GCT | AGA | TTG | TTT | ATA | GGT | GGT | AAA | AAA | GTT | GGC | 360 |
| Pro | Asn | Val | Asp 110 | Ala | Arg | Leu | Phe | Ile 115 | Gly | Gly | Lys | Lys | Val | Gly 120 | |
| ATT | AAT | CCT | AAA | ATT | AAT | AAT | TTA | ATG | CCA | GGA | TAT | GAA | GTT | GCA | 405 |
| Ile | Asn | Pro | Lys 125 | Ile | Asn | Asn | Leu | Met 130 | Pro | Gly | Tyr | Glu | Val | Ala 135 | |
| AAG | TAT | GAT | CTT | ATA | TGG | ATT | TGT | GAT | AGT | GGA | ATA | AGA | GTA | ATT | 450 |
| Lys | Tyr | Asp | Leu 140 | Ile | Trp | Ile | Cys | Asp 145 | Ser | Gly | Ile | Arg | Val | Ile 150 | |
| CCA | GAT | ACG | CTT | ACT | GAC | ATG | GTG | AAT | CAA | ATG | ACA | GAA | AAA | GTA | 495 |
| Pro | Asp | Thr | Leu 155 | Thr | Asp | Met | Val | Asn 160 | Gln | Met | Thr | Glu | Lys | Val 165 | |
| GGC | TTG | GTT | CAC | GGG | CTG | CCT | TAC | GTA | GCA | GAC | AGA | CAG | GGC | TTT | 540 |
| Gly | Leu | Val | His 170 | Gly | Leu | Pro | Tyr | Val 175 | Ala | Asp | Arg | Gln | Gly | Phe 180 | |
| GCT | GCC | ACC | TTA | GAG | CAG | GTA | TAT | TTT | GGA | ACT | TCA | CAT | CCA | AGA | 585 |
| Ala | Ala | Thr | Leu 185 | Glu | Gln | Val | Tyr | Phe 190 | Gly | Thr | Ser | His | Pro | Arg 195 | |
| TAC | TAT | ATC | TCT | GCC | AAT | GTA | ACT | GGT | TTC | AAA | TGT | GTG | ACA | GGA | 630 |
| Tyr | Tyr | Ile | Ser 200 | Ala | Asn | Val | Thr | Gly 205 | Phe | Lys | Cys | Val | Thr | Gly 210 | |
| ATG | TCT | TGT | TTA | ATG | AGA | AAA | GAT | GTG | TTG | GAT | CAA | GCA | GGA | GGA | 675 |
| Met | Ser | Cys | Leu | Met 215 | Arg | Lys | Asp | Val | Leu 220 | Asp | Gln | Ala | Gly | Gly 225 | |
| CTT | ATA | GCT | TTT | GCT | CAG | TAC | ATT | GCC | GAA | GAT | TAC | TTT | ATG | GCC | 720 |
| Leu | Ile | Ala | Phe | Ala 230 | Gln | Tyr | Ile | Ala | Glu 235 | Asp | Tyr | Phe | Met | Ala 240 | |
| AAA | GCG | ATA | GCT | GAC | CGA | GGT | TGG | AGG | TTT | GCA | ATG | TCC | ACT | CAA | 765 |
| Lys | Ala | Ile | Ala | Asp 245 | Arg | Gly | Trp | Arg | Phe 250 | Ala | Met | Ser | Thr | Gln 255 | |
| GTT | GCA | ATG | CAA | AAC | TCT | GGC | TCA | TAT | TCA | ATT | TCT | CAG | TTT | CAA | 810 |
| Val | Ala | Met | Gln | Asn 260 | Ser | Gly | Ser | Tyr | Ser 265 | Ile | Ser | Gln | Phe | Gln 270 | |
| TCC | AGA | ATG | ATC | AGG | TGG | ACC | AAA | CTA | CGA | ATT | AAC | ATG | CTT | CCT | 855 |
| Ser | Arg | Met | Ile | Arg 275 | Trp | Thr | Lys | Leu | Arg 280 | Ile | Asn | Met | Leu | Pro 285 | |
| GCT | ACA | ATA | ATT | TGT | GAG | CCA | ATT | TCA | GAA | TGC | TTT | GTT | GCC | AGT | 900 |
| Ala | Thr | Ile | Ile | Cys 290 | Glu | Pro | Ile | Ser | Glu 295 | Cys | Phe | Val | Ala | Ser 300 | |
| TTA | ATT | ATT | GGA | TGG | GCA | GCC | CAC | CAT | GTG | TTC | AGA | TGG | GAT | ATT | 945 |
| Leu | Ile | Ile | Gly | Trp 305 | Ala | Ala | His | His | Val 310 | Phe | Arg | Trp | Asp | Ile 315 | |
| ATG | GTA | TTT | TTC | ATG | TGT | CAT | TGC | CTG | GCA | TGG | TTT | ATA | TTT | GAC | 990 |
| Met | Val | Phe | Phe | Met 320 | Cys | His | Cys | Leu | Ala 325 | Trp | Phe | Ile | Phe | Asp 330 | |
| TAC | ATT | CAA | CTC | AGG | GGT | GTC | CAG | GGT | GGC | ACA | CTG | TGT | TTT | TCA | 1035 |
| Tyr | Ile | Gln | Leu | Arg 335 | Gly | Val | Gln | Gly | Gly 340 | Thr | Leu | Cys | Phe | Ser 345 | |
| AAA | CTT | GAT | TAT | GCA | GTC | GCC | TGG | TTC | ATC | CGC | GAA | TCC | ATG | ACA | 1080 |
| Lys | Leu | Asp | Tyr | Ala 350 | Val | Ala | Trp | Phe | Ile 355 | Arg | Glu | Ser | Met | Thr 360 | |
| ATA | TAC | ATT | TTT | TTG | TCT | GCA | TTA | TGG | GAC | CCA | ACT | ATA | AGC | TGG | 1125 |
| Ile | Tyr | Ile | Phe | Leu 365 | Ser | Ala | Leu | Trp | Asp 370 | Pro | Thr | Ile | Ser | Trp 375 | |

```
AGA  ACT  GGT  CGC  TAC  AGA  TTA  CGC  TGT  GGG  GGT  ACA  GCA  GAG  GAA        1170
Arg  Thr  Gly  Arg  Tyr  Arg  Leu  Arg  Cys  Gly  Gly  Thr  Ala  Glu  Glu
               380                    385                         390

ATC  CTA  GAT  GTA  TAA CTACAG CTTTGTGAC TGTATATAA GGAAA              1215
Ile  Leu  Asp  Val

AAAGAGAAGT  ATTATAAATT  ATGTTTATAT  AAATGCTTTT  AAAAATCTAC            1265

CTTCTGTAGT  TTTATCACAT  GTATGTTTTG  GTATCTGTTC  TTTAATTTAT            1315

TTTTGCATGG  CACTTGCATC  TGTGAAAAAA  AA                                1347
```

( 2 ) INFORMATION FOR SEQ ID NO:2:

( i ) SEQUENCE CHARACTERISTICS:
        ( A ) LENGTH: 394 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Met  Ala  Leu  Leu  Asp  Leu  Ala  Leu  Glu  Gly  Met  Ala  Val  Phe  Gly
 1               5                    10                         15

Phe  Val  Leu  Phe  Leu  Val  Leu  Trp  Leu  Met  His  Phe  Met  Ala  Ile
               20                    25                         30

Ile  Tyr  Thr  Arg  Leu  His  Leu  Asn  Lys  Lys  Ala  Thr  Asp  Lys  Gln
               35                    40                         45

Pro  Tyr  Ser  Lys  Leu  Pro  Gly  Val  Ser  Leu  Lys  Pro  Leu  Lys
               50                    55                         60

Gly  Val  Asp  Pro  Asn  Leu  Ile  Asn  Asn  Leu  Glu  Thr  Phe  Phe  Glu
                    65                    70                         75

Leu  Asp  Tyr  Pro  Lys  Tyr  Glu  Val  Leu  Leu  Cys  Val  Gln  Asp  His
                    80                    85                         90

Asp  Asp  Pro  Ala  Ile  Asp  Val  Cys  Lys  Lys  Leu  Leu  Gly  Lys  Tyr
                    95                   100                        105

Pro  Asn  Val  Asp  Ala  Arg  Leu  Phe  Ile  Gly  Gly  Lys  Lys  Val  Gly
                   110                   115                        120

Ile  Asn  Pro  Lys  Ile  Asn  Asn  Leu  Met  Pro  Gly  Tyr  Glu  Val  Ala
                   125                   130                        135

Lys  Tyr  Asp  Leu  Ile  Trp  Ile  Cys  Asp  Ser  Gly  Ile  Arg  Val  Ile
                   140                   145                        150

Pro  Asp  Thr  Leu  Thr  Asp  Met  Val  Asn  Gln  Met  Thr  Glu  Lys  Val
                   155                   160                        165

Gly  Leu  Val  His  Gly  Leu  Pro  Tyr  Val  Ala  Asp  Arg  Gln  Gly  Phe
                   170                   175                        180

Ala  Ala  Thr  Leu  Glu  Gln  Val  Tyr  Phe  Gly  Thr  Ser  His  Pro  Arg
                   185                   190                        195

Tyr  Tyr  Ile  Ser  Ala  Asn  Val  Thr  Gly  Phe  Lys  Cys  Val  Thr  Gly
                   200                   205                        210

Met  Ser  Cys  Leu  Met  Arg  Lys  Asp  Val  Leu  Asp  Gln  Ala  Gly  Gly
                   215                   220                        225

Leu  Ile  Ala  Phe  Ala  Gln  Tyr  Ile  Ala  Glu  Asp  Tyr  Phe  Met  Ala
                   230                   235                        240

Lys  Ala  Ile  Ala  Asp  Arg  Gly  Trp  Arg  Phe  Ala  Met  Ser  Thr  Gln
                   245                   250                        255

Val  Ala  Met  Gln  Asn  Ser  Gly  Ser  Tyr  Ser  Ile  Ser  Gln  Phe  Gln
                   260                   265                        270

Ser  Arg  Met  Ile  Arg  Trp  Thr  Lys  Leu  Arg  Ile  Asn  Met  Leu  Pro
```

-continued

|  |  |  |  | 275 |  |  |  | 280 |  |  |  | 285 |
|---|---|---|---|---|---|---|---|---|---|---|---|---|
| Ala | Thr | Ile | Ile | Cys 290 | Glu | Pro | Ile | Ser Glu 295 | Cys | Phe | Val | Ala Ser 300 |
| Leu | Ile | Ile | Gly | Trp 305 | Ala | Ala | His | His Val 310 | Phe | Arg | Trp | Asp Ile 315 |
| Met | Val | Phe | Phe | Met 320 | Cys | His | Cys | Leu Ala 325 | Trp | Phe | Ile | Phe Asp 330 |
| Tyr | Ile | Gln | Leu | Arg 335 | Gly | Val | Gln | Gly Gly 340 | Thr | Leu | Cys | Phe Ser 345 |
| Lys | Leu | Asp | Tyr | Ala 350 | Val | Ala | Trp | Phe Ile 355 | Arg | Glu | Ser | Met Thr 360 |
| Ile | Tyr | Ile | Phe | Leu 365 | Ser | Ala | Leu | Trp Asp 370 | Pro | Thr | Ile | Ser Trp 375 |
| Arg | Thr | Gly | Arg | Tyr 380 | Arg | Leu | Arg | Cys Gly 385 | Gly | Thr | Ala | Glu Glu 390 |
| Ile | Leu | Asp | Val |  |  |  |  |  |  |  |  |  |

( 2 ) INFORMATION FOR SEQ ID NO:3:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( x i ) SEQUENCE DESCRIPTION: SEQ ID NO:3:

ATCATATGGC GCTGGACCTG GC    22

( 2 ) INFORMATION FOR SEQ ID NO:4:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( x i ) SEQUENCE DESCRIPTION: SEQ ID NO:4:

CAATCTAGCA TCAACATTTG GATA    24

CERAMIDE GLUCOSYLTRANSFERASE

BACKGROUND OF THE INVENTION

1. Field of the Invention

The present invention relates to sugar transferases and the genes encoding said enzymes. More specifically, the present invention relates to ceramide glucosyltransferases, i.e., glucosylceramide synthetases catalyzing glucose transfer, and to genes encoding the enzymes.

2. Description of Related Art

Glycosphingolipids (GSLs) are a class of membrane components that have the lipid portion embedded in the outer leaflet of the lipid bilayer of plasma membrane and the sugar chains extended to the outer environment. Glycosphingolipids exist essentially in all of the animal cells and are suggested as being important substances responsible for various cellular processes such as differentiation, adhesion, proliferation, and cell-cell recognition (Varki, A., Glycobiology, 3, pp.97–130, 1993).

With only a few exceptions, almost all of the glycolipids are synthesized from glucosylceramide as a precursor that is produced by the transfer of glucose to ceramide. Ceramide glucosyltransferase (UDP-glucose: ceramide β1-1' glucosyltransferase, GlcT-1, EC2.4.1.80: hereinafter in the specification, this enzyme is occasionally referred to simply as "ceramide glucosyltransferase.") catalyzes the first glycosylation step of the glycosphingolipid biosyntheses, i.e., the transfer of glucose from UDP-Glc to ceramide (Basu, S. et al., J. Biol. Chem., 243, pp.5802–5807, 1968). Glucosylceramide (GlcCer), the product of this enzyme, serves as precursors for more than 300 of glycosphingolipid biosyntheses (Radin, N. S., Nuerochem. Res., 5, pp.533–540, 1994).

GlcT-1 was first discovered from embryonic chick brain (Basu, S. et al., J. Biol. Chem., 243, pp.5802–5807, 1968). However, the properties of the enzyme have not been fully studied, because of the difficulties in assaying and purifying the enzyme. Only limited data have been published concerning GlcT-1 so far, e.g. successful solubilization of the enzyme from rat Golgi fraction (Durieux, I. et al., Biochem. Biophys. Acta, 1024, pp.263–266, 1990) and discovery of the enzymes in liver and brain each characterized by distinguishable properties (Vunnam, R. et al., Biochem. Biophys. Acta, 573, pp.73–82, 1979). It has recently been revealed that the synthesis of GlcCer occurs at the cytosolic surface of Golgi apparatus, while other glycosylation reactions in biosynthetic pathways of glycosphingolipid take place at the lumenal side of the organelle. However, the most of enzymatic properties of the ceramide glucosyltransferases remain unknown. As for ceramide galactosyltransferase, having a similar catalytic activity, the cloning of the enzyme was reported (Schulte, S. et al., Proc. Natl. Acad. Sci. USA, 90, pp.10265–10269, 1993).

SUMMARY OF THE INVENTION

An object of the present invention is to provide ceramide glucosyltransferases derived from mammals, preferably from human. Another object of the present invention is to provide the genes encoding said ceramide glucosyltransferases.

The inventors of the present invention previously reported the isolation and characterization of a mouse melanoma B16 mutant, GM-95, deficient in ceramide glucosyltransferases (Nozue, M. et al., Int. J. Cancer, 42, pp.734–738, 1988; Ichikawa, S. et al., Proc. Natl. Acad. Sci. USA, 91, pp.2703–2707, 1994). By an expression cloning technique using the deficient mutant cell, GM-95 as a recipient cell, the inventors succeeded in isolating the cDNA encoding human ceramide glucosyltransferase (UDP-glucose; N-acylsphingosine D-glucosyltransferase, EC 2.4.1.80).

In one aspect, the present invention provides the human ceramide glucosyltransferase characterized by the amino-acid sequence (amino acids from No.1 to 394) of SEQ. ID. No.2 disclosed in the sequence listing. In another aspect, the present invention provides the gene encoding said human ceramide glucosyltransferase, and as its preferred embodiment, the ceramide glucosyltransferase gene characterized by from nucleotide No.1 to 1185 (including the terminal codon) of the nucleic acid sequence of SEQ. ID. No.1 disclosed in the sequence listing. The enzyme of the present invention has activity of catalyzing glucose transfer from UDP-Glc to ceramide.

BRIEF DESCRIPTION OF THE DRAWINGS

FIG. 2(A) and FIG. 2(B) show the amino acid sequence of the human GlcT-1 as a preferred embodiment of the ceramide glucosyltransferase of the present invention.

DETAILED DESCRIPTION OF THE PREFERRED EMBODIMENTS

Figure 1:
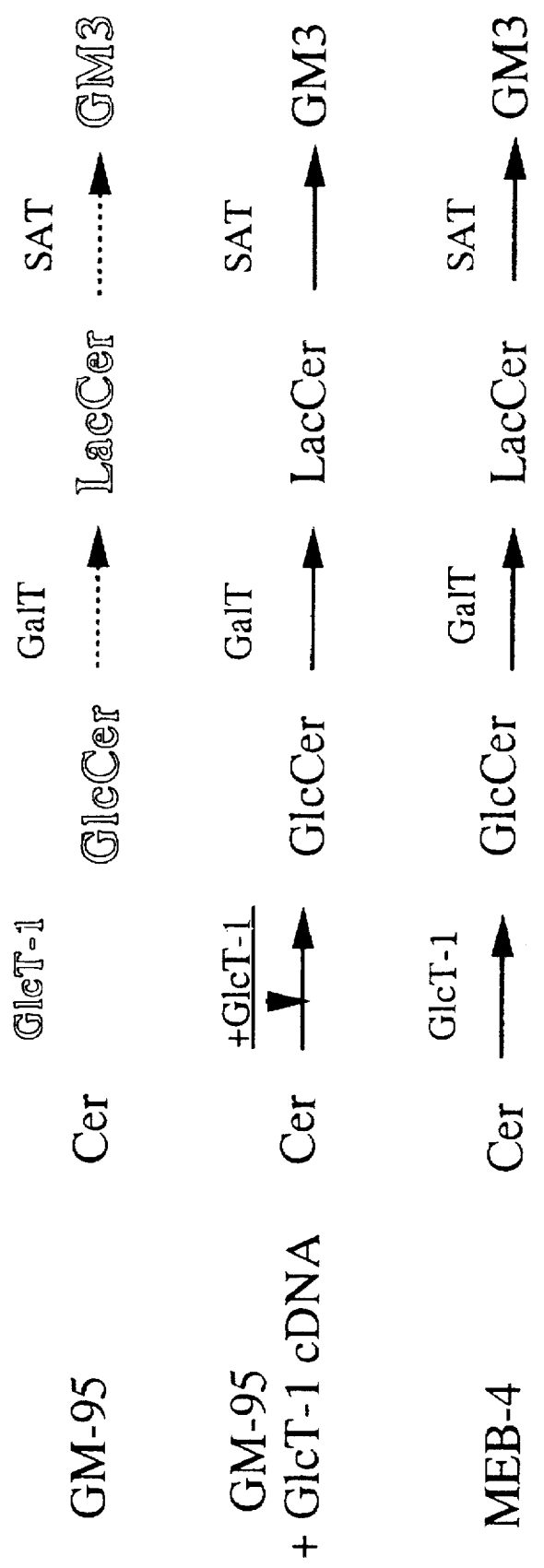
FIG. 1 shows the synthetic pathway of glycosphingolipids. Open letters indicate enzymes and glycosphingolipids deficient in GM-95 cells. Broken arrows represent reactions that do not proceed in GM-95 cells due to the deficiency of substrates. Cer, ceramide; GalT, UDP-galactose: glucosylceramide galactosyltransferase; and SAT, CMP-sialic acid: lactosylceramide sialyltransferase.
Figure 3:
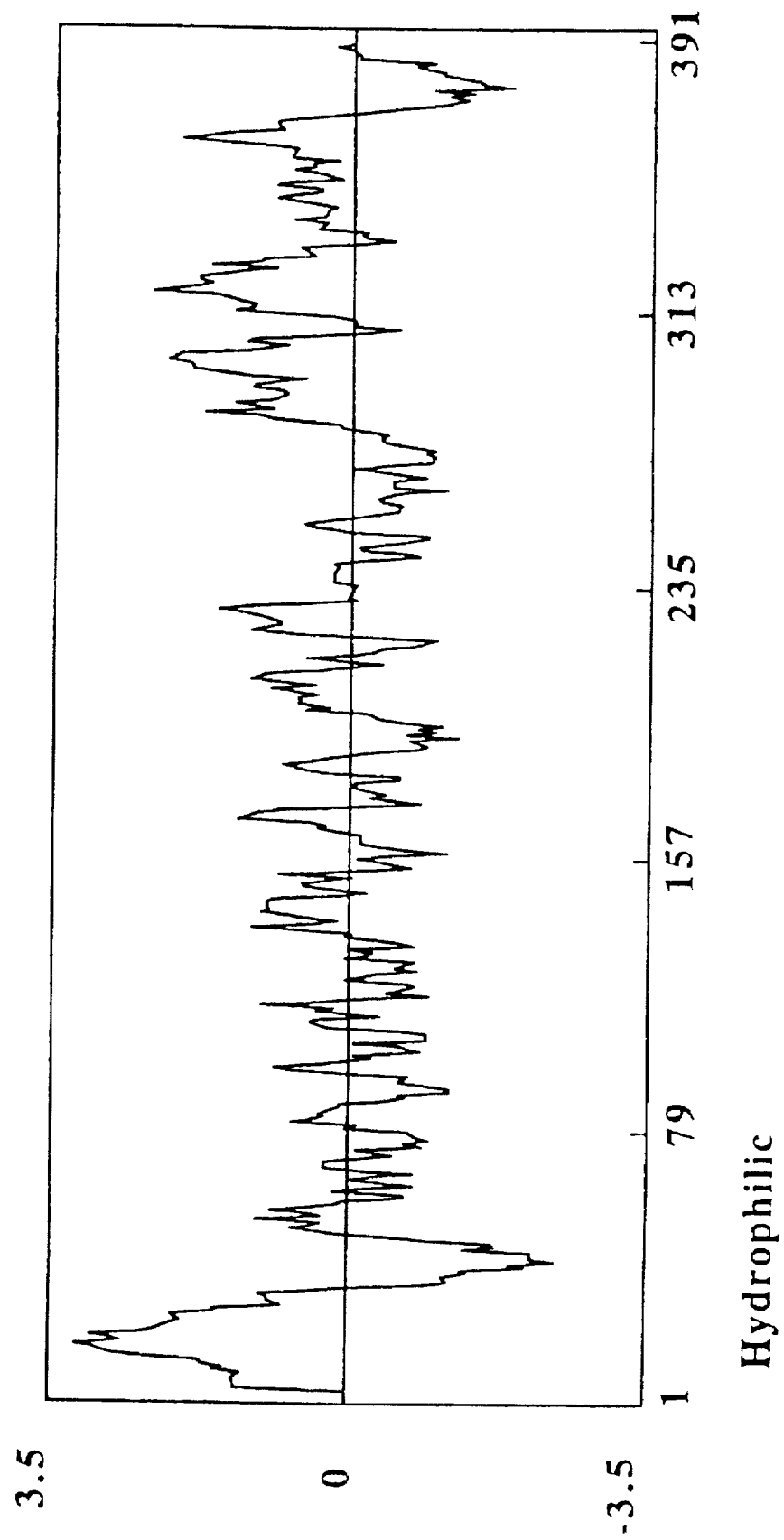
FIG. 3 shows hydropathy plot of the amino acid sequence of the human GlcT-1 as a preferred embodiment of the ceramide glucosyltransferase of the present invention. In the figure, positive values represent increased hydrophobicity and negative values increased hydrophilicity.

Besides the naturally derived human enzyme described above, any one of the enzymes, which has activity of catalyzing glucose transfer from UDP-Glc to ceramide and is characterized by a modified amino acid sequence in which the amino acid sequence defined by SEQ. ID. No.2 is inserted, deleted, and/or substituted with one or more amino acid residues, also falls within the scope of the ceramide glucosyltransferase of the present invention. Among these enzymes, naturally derived enzymes that are being expressed in mammals such as humans, monkeys, dogs, cats, cows, horses, rats, and mice are preferred.

In further aspect, the present invention also provides a class of polypeptides each of which comprises the amino acid sequence of any one of the above-described enzymes therein and has activity of catalyzing glucose transfer from UDP-Glc to ceramide. These polypeptides are characterized to have the full length of the amino acid sequence of the above-described enzyme as a part of their entire polypeptide sequences. In addition, another class of polypeptides is also provided which has activity of catalyzing glucose transfer from UDP-Glc to ceramide and comprises, as a part or the whole thereof, an amino acid sequence that is a portion of the amino acid sequence of the above-described enzyme and responsible for glucose transfer from UDP-Glc to ceramide (i.e., so called an enzymatically active domein). These polypeptides comprise, as a part or the whole thereof, the active domain derived from the above-described enzyme as a part thereof.

For example, a polypeptide, which is obtainable by selectively removing a transmembrane domain (hydrophobic domein) and ligating a resulting active domain with a signal peptide, is expected to be useful as a soluble enzyme in an extracellularly releasable form. For a determination of the hydrophobic domain, methods well known to one of ordinary skilled artisan may be applied, which include, for example, the method of Kyte et al. (Kyte. J. et al., J. Mol. Biol., 157, pp.105–132, 1982) and the method of Hopp & Woods.

According to another aspect of the present invention, nucleotide sequences encoding any one of the above-described ceramide glucosyltransferase and those encoding any one of the above polypeptides. Examples include, any one of genes encoding the above-described human ceramide glucosyltransferase and, as a preferred example thereof, the gene characterized by nucleotide No.1 to 1185 (including the terminal codon) of the nucleic acid sequence of SEQ. ID. No.1 disclosed in the sequence listing; and a modified nucleic acid sequence encoding a polypeptide capable of catalyzing glucose transfer from UDP-Glc to ceramide in which the the nucleic acid sequence of SEQ. ID. No.1 is inserted, deleted, and/or substituted with one or more nucleic acids, all of which fall within the scope of the genes of the present invention. DNA sequences comprising any one of the aforementioned nucleotide sequences as a part thereof also fall within the scope of the present invention.

Among the genes of the present invention, the gene encoding the human ceramide glucosyltransferase can readily be obtained by one of ordinary skilled in the art according to the processes detailed in the examples set out below in the specification or by referring to the disclosed processes, or alternatively, by optionally applying appropriate alterations or modifications thereto. In addition, ceramide glucosyltransferases derived from mammals other than human can also be obtained according to the exemplified processes by suitably choosing readily available experimental materials. The genes of the present invention are useful for diagnostic probes to evaluate expression of the above enzyme in a living body, as well as for the manufacture of the aforementioned enzymes and polypeptides.

In further aspect, the present invention provides a recombinant vector comprising any one of the aforementioned genes or the DNA sequences, and a transformant cell that is transformed with said recombinant vector. Types of vectors are not particularly limited and any vectors may be used so far as they are available in the art. Preferably, types of vectors may be appropriately chosen depending on a type of a host cell to be transformed. Types of host cells are also not particularly limited and any types of cells may be used, such as, procaryotic cells including bacteria, e.g. *Escherichia coli*, or eucaryotic cells including animal cells or plant cells. An expression system using vaccuro virus may also be used.

The present invention also provides a process for preparing any one of the aforementioned ceramide glucosyltransferases or any one of the polypeptides catalyzing glucose transfer from UDP-Glc to ceramide, which comprises the step of separating and isolating said enzyme or polypeptide from a cultivation mixture obtained by culturing the above-described transformant. Methods of such cultivations as well as methods for separation and isolation of the desired enzyme or polypeptide are well known in the art.

The present invention will be further detailed by referring to the following examples. However, the scope of the present invention is not limited to these examples.

B. EXAMPLES (1) Materials and Methods (a) Materials

Monoclonal antibody M2590 (anti-GM3; IgM. Hirabayashi, Y. et al., J. Biol. Chem., 260, pp.13328–13333, 1985) was purchased from Meiji Seika Co. Ltd. Tokyo, Japan. Anti-mouse IgM goat IgG fraction (μ chain specific) was obtained from Organon Technika Corporation.

High fluorescent anti-mouse gamma globulin produced in goat was purchased from Antibodies Incorporated (CA. USA). Lipofectin and G418 were obtained from Life Tech. Oriental (Tokyo, Japan). The pET system was from Takara Shuzo Co., LTD. (Kyoto, Japan; Studier, F. et al., Method in Enzymol., 185, pp.60–89, 1990).

Bis-(sulfosuccinimidyl) suberate, a bifunctional cross-linker, was obtained from PIERCE (IL, USA). 6-(((N-7-nitrobenz-2-oxa-1,3-diazol-4-yl)-amino)-caproyl)-sphingosine, $C_6$-NBD-Cer, was from Molecular Probes Inc. (OR, USA). pPSVE-PyE plasmid, which carries the early region of polyoma virus, was generous gift from Dr. M. Fukuda (La Jolla Cancer Research Foundation, La Jolla, Calif.; Bierhuizen, M. F. et al., Genes and Dev., 7. pp.468–478, 1993). All other reagents were of analytical grade.

(b) cDNA Library

A cDNA library of a human melanoma cell line SK-Mel-28 was a gift from Dr. M. Fukuda (La Jolla Cancer Research Foundation, La Jolla, Calif.). The library was prepared from poly (A)$^+$ RNA by the method of Seed et al. (Seed. B. et al., Proc. Natl. Acad. Sci. USA, 84, pp.3365–3369, 1987) using pcDNAI (Invitrogen, Calif.) as a mammalian expression vector. The library contained $2.5 \times 10^6$ independent clones in *E. coli* strain MC1061/P3.

(c) Cell Lines and Culture Conditions

GM-95, a B16 melanoma mutant that does not express GlcT-1, was established according to reported methods (Nozue. M. et al., Int. J. Cancer, 42, pp.734–738, 1988; Ichikawa, S. et al., Proc. Natl. Acad. Sci. USA, 91, pp.2703–2707, 1994). GM-95-PyT, a recipient cell line for transient expression, was established by cotransfection of GM-95 with pSV2neo plasmid and pPSVE-PyE plasmid (Bierhuizen, M. F. et al., Genes and Dev., 7, pp.468–478, 1993), followed by the selection with G418. The cells were ordinarily maintained in Dulbecco's modified Eagle medium, or in DMEM (Gibco Laboratories, NY) supplemented with 10% fetal calf serum (FCS) under 5% $CO_2$.

(d) Isolation of a cDNA by Complementation

Plasmids that carry cDNAs were prepared from an amplified portion of the cDNA library. GM-95-PyT cells were transfected with the plasmid DNA by electroporation (Chu, G. et al., Nucleic Acids Res., 15, pp.1311–1326, 1987). Outlines of the procedures were as follows: $2 \times 10^7$ GM-95-PyT cells were washed with K-PBS$^-$ (30.8 mM NaCl, 120.7 mM KCl, 8.1 mM $Na_2HPO_4$, and 1.46 mM $KH_2PO_4$), and suspended in 400 μl of K-PBS$^-$ supplemented with 5 mM $MgCl_2$ (K-PBS$^+$). Plasmid DNA (100 μg) dissolved in 400 μl K-PBS$^+$ was added to the cell suspension and the mixture was incubated on ice for 10 min. Cells were transferred to 0.4 cm cubette and exposed to a 300 V pulse with a capacitance of 960 μF by Gene Pulsar (Bio Rad). Then, the cells were again cooled on ice.

After 10 min, the cell suspension was diluted with 5 ml of cold serum-free DMEM and incubated for 30 min at 25° C. The cells were then inoculated in culture dishes and cultured at 37° C. in DMEM supplemented with 20% FCS. A total of $1 \times 10^8$ cells was transfected as above, and cultured in five 15 cm culture dishes. After sixty hours, the cells were detached from the plate by incubation with 5 ml per plate of PBS containing 5 mM EDTA. The cells were resuspended at a concentration of $5 \times 10^7$ cells/ml in PBS-EDTA-NaN$_3$ (PBS containing 5% FBS, 0.02% sodium azide, and 0.5 mM EDTA) and then subjected to a reaction with M2590 mAb (20 μg/ml) for 2 hrs on ice. After the reaction, cells were washed twice with ice-cooled PBS, resuspended in PBS containing 50 mM HEPES buffer (pH 8.3) and 0.2 mM BS$_3$ at a concentration of $1 \times 10^7$ cells/ml, and incubated for 30 min on a ice-bath.

After then, the cells were washed twice with ice-cooled PBS, resuspended in 10 ml of PBS-EDTA-NaN$_3$, and divided into five 6 cm panning plate coated with anti-mouse IgM goat IgG (μ chain specific, Wysocki, L. et al., Proc. Natl. Acad. Sci. USA, 75, pp.2844–2848, 1978). After incubation for 4 h at 25 °C., non-adherent cells were removed by gentle washing with PBS-EDTA-NaN$_3$. The plasmids were extracted from the adherent cells by the method of Hirt et al. (Hirt, B., J. Mol. Biol., 26, pp.365–369, 1967) and introduced into E. coli., MC1061/P3 by electroporation. The plasmids were prepared from 500 ml of 2×YT (Maniatis, T. et al., Molecular Cloning: A Laboratory Manual, Cold Spring Harbor Laboratory Press, Plainview, N.Y.), and another round of panning was performed as described above. After the second round of panning, 500 E. coli clones were divided into 32 pools and plasmids were prepared from each pool by mini preparation (Maniatis, T. et al. as described above).

The plasmids were introduced into GM-95-PyT cells cultured in 24 well plates by the DEAE dextran method (Sussman, D. J. et al., Mol. Cell Biol., 4, pp.1641, 1984) and the cells were cultured for 60 h. The cells were then harvested from each of the wells and the GlcT-1 activity was measured. Two pools were found to be positive.

The 62 individual E. coli clones from the positive pools were examined as described above and a ceramide glucosyltransferase cDNA was isolated. The clone was designated as pCG-1.

(e) Stable Expression of GlcT-1 in GM-95 Cells pCG-1 or pcDNAI was co-transfected with pSV2neo using lipofection (Felgner, P. L. et al., Proc. Natl. Acad. Sci. USA, 84, pp.7413–7417, 1987) as described below. By using 10 cm tissue culture dishes, GM-95 cells were cultured in 10 ml DMEM supplemented with 10% FCS until they reached 50% confluency. The medium was replaced with 10 ml serum-free DMEM, and then, 300 μl of water mixed with pCG-1 (60 μg), pSV2neo (6 μg), and Lipofectin (150 μg) was added to the culture. As a control, pcDNAI vector being lack of the insert was used instead of pCG-1. The next day, the cells were subjected to selection in a medium containing 800 g g/ml of G418. After two weeks, more than 100 colonies were obtained from each of the plates. The cells were detached from the plates, mixed and replaced on new plates. The cells were maintained for two months in the medium containing G418 and used for flow-cytometry or lipid analyses without cloning.

(f) Expression of GlcT-1 in E. coli

The cDNA from pCG-1 was cloned into the EcoRI site of Bluescript KS vector to locate BamHI site at the 3' end (pCG-2). An NdeI site was introduced at the ATG codon of the GlcT-1 open-reading frame by standard PCR methods (Felgner, P. L. et al., Proc. Natl. Acad. Sci. USA, 84, pp.7413–7417, 1987) using primers, i.e. 5'-ATCATATGGCGCTGGACCTGGC-3' (SEQ ID NO.3) and 5'-CAATCTAGCATCAACATTTGGATA-3' (SEQ ID NO. 4). The resulting 300 bp-fragment was digested with HindIII and cloned into the SmaI-HindIII region of pUC119.

After amplification, the fragment was recovered by digestion with KpnI and HindIII. The fragment was then ligated to 1.1 kb KpnI-HindIII fragment of pCG-2 to afford pCG-3.

Then, the full-length cDNA having NdeI and BamHI sites, that was derived from pCG-3, was cloned into E. coli expression vector pET-3a (Studier, F. et al., Method in Enzymol., 185, pp.60–89, 1990). The resulting plasmid pET-CG1 was transformed into the E. coli strain BL21 (DE3) (Studier, F. et al., ibid., 185, pp.60–89, 1990). For the expression of the cloned GlcT-1, E. coli cells harboring the plasmids were grown in NZCYM medium at 37° C. (Maniatis, T. et al. as described above). When cell density was reached 0.25 OD$_{600}$, isopropyl-β-thiogalactopyranoside (IPTG) was added to a final concentration of 1 mM and the cells were incubated for an additional 5 hours. After the incubation, the cells were harvested and then disrupted by sonication. 150 μg of cell lysate was used for an enzyme assay, and an incubation was performed for 7 h. Other conditions were in accordance with the standard assay conditions.

(g) Nucleotide Sequence Determination

The plasmid containing human GlcT-1 cDNA was treated with exonucleaseIII and mung bean nuclease to construct nested deletion clones of various lengths (Heinkoff, S., Gene, 28, pp.351–359, 1984). Nucleotide sequences were determined in both directions by either the dideoxynucleotide chain termination method using BucaBEST (Takara Shuzo, Co., LTD, Kyoto, Japan; Sanger, F., et al., Proc. Natl. Acad. Sci. USA, 74, pp.5463–5467, 1977) or the cycle sequencing methods using Taq DNA polymerase. Applied Biosystems model 373 A and Pharmacia A.L.F.DNA sequencers were used for the analyses. Some analyses were performed at the Takara Shuzo customer service center.

(h) DNA Manipulation

DNA manipulation was carried out according to the method of Maniatis et al. (Maniatis, T., as described above).

(i) Flow Cytometry

Cells were detached from culture dishes using PBS containing 5 mM EDTA and then reacted with M2590 mAb (20 μg/ml in PBS-EDTA-NaN$_3$) for 2 h on an ice bath. The cells were washed with PBS and reacted with FITC labeled anti-mouse immunoglobulin for 3 h on ice. After washing with PBS, the cells were analyzed by FACStar (product of Beckton Dickinson).

(j) Lipid Analyses

Cells were collected by scraping at subconfluency, washed twice with PBS and lyophilized. Total lipids were extracted with 20 volumes of chloroform:methanol (2:1, v/v), filtered, and concentrated to dryness under reduced pressure. The total lipids were then again dissolved in a small volume of chloroform:methanol (2:1, v/v) and chromatographed on a precoated silica-gel TLC plate (E. Merck) using chloroform:methanol:water (65:25:4, v/v).

Glycosphigolipids (GSLs) were visualized with orcinol-HCl reagent.

(k) Enzyme Assay

GlcT-1 activity was assayed according to the method of Lipsky et al. (Lipsky, N. G. et al., J. Cell. Biol., 100, pp.27–34, 1986) with slight modifications. C$_6$-NBD-Cer, a synthetic fluorescent substrate, in a form of liposome was used for the assay. C$_6$-NBD-Cer (50 μg) and lecithin (500 μg) were mixed in 100 μl ethanol and the solvent was removed to dryness. After 1 ml of water was added to the residue, liposomes were prepared by sonication. A standard reaction mixture [100 μl; 20 mM Tris-HCl (pH 7.5)/500 μM UDP-Glc/20 μl liposomes/50 μg cell protein as enzyme source] was incubated for 4 h at 30° C. After then, lipids were extracted and applied on silica-gel 60 plates. NBD lipids were separated by using $CHCl_3/CH_3OH/H_2O$ (65:25:4, v/v) and the lipids were visualized by UV illumination.

(l) Protein Assay

Proteins were assayed using Micro BCA Protein Assay Reagent Kit (PIERCE, IL, USE) according to the method of Smith et al. (Smith, P. K., et al., Anal. Biochem., 150, pp.76–85, 1985).

(m) Isolation of mRNA and Northern Blot Analysis

Poly $A^+$ RNA from each cell line was isolated by Fast Track mRNA Isolation Kit (Invitrogen Corporation) according to the manufacture's instruction. Poly $A^+$ RNA (2 μg) was subjected to electrophoresis on 1% agarose gel containing formaldehyde and transblotted onto nylon membrane (Hybond-N, Amersham, Maniatis, T. et al., as described above). A pre-made membrane was used for the analysis of mRNA from various tissues (Human Multiple Tissue Northern Blot, Clontech).

The 1.1 kb HindIII-XhoI cDNA fragment of pCG-1 was labeled with [$\alpha$-$^{32}$P] dCTP (6000 Ci/mmol, Amersham) by Multiprime DNA labelling system (Amersham) and used as a probe. Hybridization was carried out at 42° C. for 24 h in 5×SSPE [1×SSPE contains 0.18M NaCl, 10 mM $NaPO_4$ (pH7.7) and 1 mM EDTA] containing 50% formaldehyde, 2% SDS, 10×Denhart's solution, 100 μg/ml of salmon sperm DNA, and $^{32}$p labeled probe. After hybridization, the membrane was washed with 2×SSC containing 0.5% SDC and 0.1×SSC each for 40 min at 50° C.

(2) Results (a) cDNA Cloning

By using a mammalian expression cloning system developed by Seed et al. (Seed, B. et al., Proc. Natl. Acad. Sci. USA, 84, pp.3365–3364, 1987), cDNAs from a SK-Mel-28 library in the expression vector peDNAI were introduced in GM-95-PyT that lacks GlcT-1 activity. The recipient cell line GM-95-PyT, GM-95 stably expressing polyoma large T antigen, allows episomal replication of transfected plasmids. Although GM-95-PyT are deficient in GlcT-1, other enzymes involved in glycosphingolipid syntheses retained their enzymatic activities. Thus, the complementation of the GlcT-1 cDNA restores the expression of GlcCer, LacCer, and GM3 that are expressed in the parental cell line.

Three days after the transfection, cells expressing GM3 were selected by panning with the anti-GM3 mAb and petri dishes coated with anti-mouse-IgM. The binding between the mAb and GM3 was not strong enough to hold the cells on the plate, and accordingly, the bound mAb and cell surface proteins were cross-linked before the panning. Plasmids were isolated from the adherent cells and elecroporated into E. coli for further amplification. After the second round of transfection, selection, and amplification, E. coli colonies were divided into subpools and screened by a sibling selection based on the enzyme assay until a single clone pCG-1 was isolated.

(b) Transient Expression of GlcT-1 Activity in the Mutant Cells

The mutant cells transfected with pCG-1 were assayed for the GlcT-1 activities using $C_6$-NBD-ceramide as a substrate. SK-Mel-28 cells; SK-Mel-28 cells with no UDP-Glc addition; MEB-4 cells; MEB-4 cells with no UDP-Glc addition; GM-95-PyT cells; GM-95-PyT cells with no UDP-Glc addition; GM-95-PyT cells transfected with pcDNA I; GM-95-PyT cells transfected with pcDNA I with no UDP-Glc addition; GM-95-PyT cells transfected with pCG-1; GM-95-PyT cells transfected with pCG-1 with no UDP-Glc addition; $C_6$-NBD-Cer (100 pmoles); $C_6$-NBD-GlcCer (100 pmoles); and $C_6$-NBD-SM (100 pmoles) were subjected to simultaneous analysis.

As a result, GlcT-1 activity was detected in GM-95-PyT cells transfected with pCG-1, but not detected in the cells transfected with the pcDNAI vector. The production of $C_6$-NBD-GlcCer was found to be UDP-Glc dependent. GlcT-1 activities were also detected in SK-Mel-28 cells from which the library was derived as well as in the parental cell line MEB-4. A low level of NBD-GlcCer synthesis was detected due to endogenous UDP-Glc in the lysates from these two cell lines without the addition of UDP-Glc.

(c) Restoration of Glycosphingolipid Expression in the Mutant Cells Introduced with the GlcT-1 cDNA Expression of glycosphingolipid was first analyzed by flow cytometry using anti-GM3 mAb. Although a significant shift of main peak and a small population of strongly stained cells were observed in GM-95-PyT cells transfected with pCG-1, the ratio of positive population was relatively low. This was mainly due to the low transfection efficiency of GM-95-PyT cells. Accordingly, in order to produce GM-95 cells expressing GlcT-1 stably, GM-95 cells were co-transfected with pCG-1 and pSV2neo and selected with G418 for neomycin resistance, and as a result, more than 100 colonies were obtained. The cells were mixed and expanded for glycosphingolipid analysis without cloning. 75% of the cells were positively stained with GM3, and 15% were stained stronger than the parental cells.

Glycosphingolipids of the neomycin resistant cells were further analyzed by TLC followed by orcinol/$H_2SO_4$ reaction. The total lipids from $10^6$ cells were spotted onto silica-gel plate and developed with a solvent (chloroform:methanol:water=65:25:4, v/v). SK-Mel-28 cells; MEB-4 cells; GM-95 cells; GM-95 cells cotransfected with pcDNA I and pSV2neo; GM-95 cells cotransfected with pCG-1 and pSV2neo; GlcCer (2 μg); LacCer (1 μg); and GM3 (1 μg) were simultaneously analyzed, and glycosphingolipids were visualized with orcinol/$H_2SO_4$ reagent. GlcCer and GM3 were detected in the total lipids extracted from GM-95 cells carrying pCG-1 but not from the cells carrying pcDNAI.

(d) Expression of Enzymatically Active GlcT-1 in E. coli

In order to demonstrate that the isolated cDNA encodes the desired ceramide glucosyltransferase, per se, and that it does not encode a regulatory protein required for the expression of GlcT-1 activity, enzymatically active GlcT-1 was expressed in E. coli that is not capable of expressing GlcT-1 and sphingolipids including glycosphingolipids. pET3a/BL21 (DE3); pET3a/BL21 with no UDP-Glc addition; pET3a-CG1/BL21 (DE3); pET3a-CG1/BL21 (DE3) with no UDP-Glc addition; $C_6$-NBD-Cer (40 pmoles); and $C_6$-NBD-GlcCer (40 pmoles) were simultaneously analyzed. As a result, the GlcT-1 activity was detected in the cells transformed with pET-CG-1. The production of $C_6$-NBD GlcCer was observed as being UDP-Glc dependent, and no activity was detected in the cells that carried pET3a vector alone.

From these results, it is apparent that the above-mentioned cDNA encodes GlcT-1.

(e) Primary Structure of GlcT-1

FIG. 2(A) and FIG. 2(B) show the primary amino acid sequence of GlcT-1 deduced from nucleotide sequence of the cDNA. GlcT-1 consists of 394 amino acids and has a calculated molecular mass of 44,853 dalton. No significant homologies with GlcT-1 were found by searches of the DNA and protein data bases (GenBank and PIR), which revealed that GlcT-1 is a novel protein. The GC-rich sequence that precedes to the initiation codon is presumably a part of CpG island sequence that surrounds the promoters of housekeeping genes (Bird, A. P., Nature, 321, pp.209–213, 1986). The genes that contain the above sequence are usually essential for cell viability and are expressed in most cells.

The enzyme with a similar catalytic activity, ceramide galactosyltransferase (CGT), has recently been cloned (Schulte, S. et al., Proc. Natl. Acad. Sci. USA, 90, pp.10265–10269, 1993). The sequence analysis of this enzyme revealed that the enzyme was homologous to glucuronyltransferases that are participated in drug metabolic pathways. Since GlcT-1 and CGT catalyze similar reactions, it may be worth considering a possibility that these enzymes are homologous. However, no significant sequence homology was observed, which suggests that these two enzymes have different evolutionary origins. The glucuronyltransferases are expressed at the lumenal side of endoplasmic reticulam (Drake, R. R. et al., J. Biol. Chem., 267, pp.11360–11365, 1992). In contrast, GlcT-1 is a single enzyme that catalyzes the above reaction on the cytoplasmic surface, which may also support this hypothesis.

The hydropathy plot analysis (Kyte, J. et al., J. Mol. Biol., 157, pp.105–132, 1982) proved the presence of a hydrophobic segment near the N terminus that is the potential membrane-anchoring domain.

In addition, the considerable hydrophobicity was detected in the regions close to the C terminus, that may locate in the membrane.

(f) Northern Blot Analysis of GlcT-1 mRNA

The expression of GlcT-1 mRNA in melanoma cells and various human tissues was analyzed by Northern blot analysis (poly A$^+$ RNA, 2 µg). (A) the melanoma cell lines: SK-Mel-28; MEB-4; and GM-95; and (B) human tissues: heart; brain; placenta; lung; liver; skeletal muscle; kidney; and pancreas were subjected to a simultaneous analysis. Hybridization with human glyceraldehyde 3-phosphate dehydrogenase (G3PDH) cDNA was carried out as control experiments. A single transcript of 3.5 kb was detected in all of the cells and tissues examined. Strong expressions of GlcT-1 mRNA were detected in SK-Mel-28 and MEB-4 cells. Due to the deficiency of the GlcT-1, a very faint band was observed in GM-95 cells. As for human tissues, GlcT-1 mRNA expressions were observed in all of the tissues examined. In control experiments, strong expression of G3PDH mRNA was observed in skeletal muscle and heart as reported previously (Vincent, S. et al., Nucleic Acids Res., 21, pp.1498, 1993).

The ceramide glucosyltransferases of the present invention are responsible for the initial glycosylation step of glycosphingolipid biosynthesis in mammals, preferably in human. They have properties to catalyze the transfer of glucose from UCP-Glc to ceramide to afford glucosylceramide. Accordingly, the enzymes of the present invention are essential for life maintenance of mammals and are extremely valuable enzymes. In addition, the enzymes of the present invention are also useful as laboratory usable agents in the fields of biochemistry and biotechnology, as well as preparatory agents for the manufacture of pharmacologically active substances. Furthermore, they are expected to be useful as medicament for therapeutic and preventive treatment for various diseases based on reduced expression of said enzyme. The genes of the present invention are useful for a mass preparations of the above enzymes in highly purified forms, and also useful as probes that can be used for clinical tests and diagnosis of diseases based on abnormal expression of the above enzyme.

An example of the gene and the expression product thereof according to the present invention will be described in the sequence listings set out below.

What is claimed is:

1. An isolated ceramide glucosyltransferase having the amino acid sequence of SEQ ID No. 2.

2. The ceramide glucosyltransferase according to claim 1, which is encoded by the nucleotide sequence according to SEQ ID No. 1.

3. The ceramide glucosyltransferase according to claim 1, which is obtained from a mammal.

4. An isolated ceramide glucosyltransferase having the amino acid sequence of SEQ ID No. 2 and naturally occurring homologs thereof.

5. The ceramide glucosyltransferase according to claim 4, which is obtained from a mammal selected from the group consisting of human, monkey, dog, cat, cow, horse, rat and mice.

6. An isolated ceramide glucosyltransferase having the amino sequence of SEQ ID No. 2, which amino acid sequence may have one or more conservative substitutions that do not substantially alter the activity of said ceramide glucosyltransferase.

7. An isolated polypeptide comprising a fragment of the amino acid sequence of SEQ ID No. 2 which possesses glucosyltransferase activity.

8. An isolated fragment of the amino acid sequence of SEQ ID No. 2 which possesses glucosyltransferase activity.

9. An isolated fragment of the amino acid sequence of SEQ ID No. 2 which possesses glucosyltransferase activity, and naturally occurring homologs thereof.

10. The fragment according to claim 9, which is obtained from a mammal selected from the group consisting of human, monkey, dog, cat, cow, horse, rat and mice.

11. An isolated fragment of the amino acid sequence of SEQ ID No. 2, which amino acid sequence may have one or more conservative substitutions that do not substantially alter the activity of said ceramide glucosyltransferase.

12. An isolated polypeptide comprising a fragment of the amino acid sequence of SEQ ID No. 2 which possesses glucosyltransferase activity together with at least one signal peptide.

* * * * *